United States Patent
Chen et al.

(10) Patent No.: US 11,623,913 B2
(45) Date of Patent: Apr. 11, 2023

(54) METHOD OF SYNTHESIZING (1R,2R)-NITROALCOHOL COMPOUND

(71) Applicant: Sichuan University, Sichuan (CN)

(72) Inventors: Fener Chen, Sichuan (CN); Lin Dong, Sichuan (CN); Yingqi Xia, Sichuan (CN); Pei Tang, Sichuan (CN); Youcai Xiao, Sichuan (CN)

(73) Assignee: Sichuan University, Chengdu (CN)

( * ) Notice: Subject to any disclaimer, the term of this patent is extended or adjusted under 35 U.S.C. 154(b) by 200 days.

(21) Appl. No.: 16/830,037

(22) Filed: Mar. 25, 2020

(65) Prior Publication Data
US 2021/0179536 A1 Jun. 17, 2021

(30) Foreign Application Priority Data
Dec. 11, 2019 (CN) .................. 201911267703.X

(51) Int. Cl.
C07C 201/12 (2006.01)
C07C 205/16 (2006.01)
B01J 31/18 (2006.01)

(52) U.S. Cl.
CPC ........... C07C 201/12 (2013.01); B01J 31/184 (2013.01); B01J 2531/16 (2013.01); C07C 205/16 (2013.01)

(58) Field of Classification Search
CPC ........................... C07C 201/12; C07C 309/75
USPC ........................................................ 568/705
See application file for complete search history.

(56) References Cited

FOREIGN PATENT DOCUMENTS

| CN | 101709313 B | 12/2011 |
| CN | 104311424 A | 1/2015 |

OTHER PUBLICATIONS

Qin et al. Chem. Eur. J. 2012, 18, 10515-10518.*
Kaldun et al. Chem. Cat. Chem 2016, 8, 1846-1856.*
Qin et al. Chem. Eur. J. 2013, 19, 16541-16644.*

* cited by examiner

*Primary Examiner* — Ana Z Muresan

(57) ABSTRACT

Disclosed is a method of synthesizing a (1R,2R)-nitroalcohol compound of formula (I), as shown in the following reaction scheme, including: subjecting a compound of formula (II) and a compound of formula (III) to a condensation reaction in an organic solvent in the presence of a copper complex generated in situ from a chiral (1S,2R)-amino alcohol ligand and a cupric salt to produce the (1R,2R)-nitroalcohol compound of formula (I), where $R^1$ and $R^2$ are defined in the same manner as that in the specification. The method involves mild reaction conditions, excellent diastereoselectivity and high chemical yield, and thus it is suitable for industrial applications.

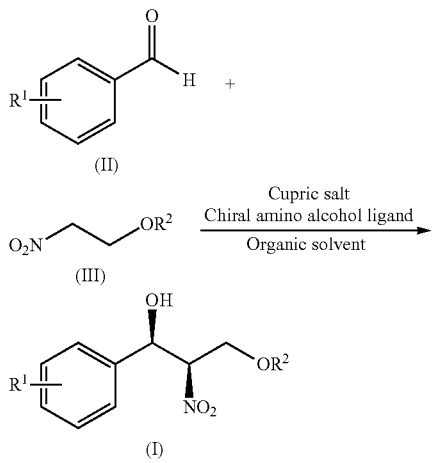

9 Claims, No Drawings

METHOD OF SYNTHESIZING (1R,2R)-NITROALCOHOL COMPOUND

CROSS-REFERENCE TO RELATED APPLICATIONS

This application claims the benefit of priority from Chinese Patent Application No. 201911267703.X, filed on Dec. 11, 2019. The content of the aforementioned application, including any intervening amendments thereto, is incorporated herein by reference in its entirety.

TECHNICAL FIELD

The present application relates to organic synthesis, and more particularly to a method of synthesizing a (1R,2R)-nitroalcohol compound of formula (I):

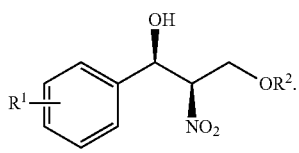

BACKGROUND OF THE INVENTION (1R,2R)-nitroalcohol compounds (I) are widely found in natural products and drug molecules due to its unique chiral structure. Currently, there are some literature associated with the preparation of chiral nitroalcohol compounds (I), but the resulting products are predominated by trans-nitroalcohol compounds. It has not been reported about the preparation of cis-nitroalcohol compounds (I).

The trans-nitroalcohol compounds are prepared mainly by asymmetric condensation of an aromatic aldehyde with a nitro compound under the catalysis of a metal-chiral ligand complex or a quinine derivative. Shibasaki et al. (*J. Am. Chem. Soc.* 2009, 131, 13860-13869) have reported a method of synthesizing the trans-nitroalcohol compounds through an asymmetric condensation of benzaldehyde with TBS-protected nitroethanol or benzyl-protected nitroethanol under the catalysis of a rubidium-sodium bimetal catalyst. Though this method has high diastereoselectivity, it is not conducive to large-scale production due to complicated operation and low reaction temperature (−40° C.). Hong et al. (*Angew. Chem. Int. Ed.* 2012, 51, 1620-1624) have disclosed an asymmetric condensation under the co-catalysis of thiourea and cobalt, in which 2-methoxybenzaldehyde can react smoothly with TBS-protected nitroethanol to give the target compound with high yield and enantioselectivity. However, the extremely-low reaction temperature (−80° C.) greatly limit its industrial application. Levacher et al. (*Chemistry Select,* 2016, 1, 3184-3188) have demonstrated that the benzaldehyde can asymmetrically condense with nitroethanol under the catalysis of quinine derivatives. However, this method fails to provide a satisfactory yield, and also shows poor diastereoselectivity and enantioselectivity, where an anti/syn ratio is 83:17, and the anti-isomer and the syn-isomer respectively have an ee value of 63% and 32%.

The above-mentioned methods are mainly employed to prepare trans-nitroalcohol compounds, and there are few reports on the preparation of cis-nitroalcohol compounds (I), limiting the research, development and production of related medicines. In the rubidium-sodium bimetal catalytic system, one acts as a Lewis acid to activate the aromatic aldehyde and the other acts as a Bronsted base to activate the nitroethanol derivative. Under such co-catalysis, the condensation reaction generally leads to the occurrence of trans products. Similarly, in the thiourea-cobalt catalytic system, thiourea and cobalt are respectively capable of activating the nitroethanol derivative and the aromatic aldehyde, and the condensation products formed using such system are also mainly trans. So far, there is no report on the preparation of cis-nitroalcohol compounds (I) using these substrates through condensation.

Therefore, there is still an urgent need to develop a method of preparing (1R,2R)-nitroalcohol compounds (I) with simple process, low cost and less pollution.

SUMMARY OF THE INVENTION

An object of the invention is to provide a method of asymmetrically synthesizing a (1R,2R)-nitroalcohol compound (I), which has advantages of simple process, low cost and less pollution, to overcome the shortcomings of the prior art.

Specifically, the invention provides a method of synthesizing a (1R,2R)-nitroalcohol compound of formula (I), comprising:

subjecting a compound of formula (II) and a compound of formula (III) to a condensation reaction in an organic solvent in the presence of a copper complex formed in situ from a chiral (1S,2R)-amino alcohol ligand and a cupric salt to produce the (1R,2R)-nitroalcohol compound of formula (I), as shown in the following reaction scheme:

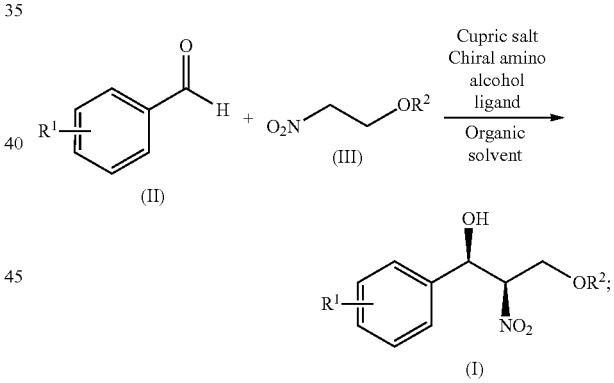

wherein:

$R^1$ is hydrogen, methyl, ethyl, linear or branched $C_3$-$C_5$ alkyl, cyclopropyl, phenyl, halogen, trifluoromethyl, nitro, cyano, linear or branched $C_1$-$C_5$ alkylthio, linear or branched $C_1$-$C_5$ alkylsulfinyl, linear or branched $C_1$-$C_5$ alkylsulfonyl, hydroxyl, methoxy, ethoxy, linear or branched $C_3$-$C_5$ alkoxy, linear or branched $C_1$-$C_5$ alkyl acyloxy or benzyloxy;

$R^2$ is hydrogen, methyl, ethyl, linear or branched $C_3$-$C_5$ alkyl, acetyl, linear or branched $C_3$-$C_5$ alkanoyl, benzoyl, benzyl, triphenylmethyl, trimethylsilyl, triethylsilyl, tri(linear or branched $C_3$-$C_5$ alkyl) silyl, di-tert-butylphenylsilyl or tert-butyldimethylsilyl.

In some embodiments, $R^1$ is hydrogen, methyl, ethyl, linear or branched $C_3$-$C_5$ alkyl, phenyl, halogen, trifluoromethyl, nitro, cyano, linear or branched $C_1$-$C_5$ alkylthio, linear or branched $C_1$-$C_5$ alkylsulfinyl, linear or branched $C_1$-$C_5$ alkylsulfonyl, methoxyl, ethoxyl, linear or branched $C_3$-$C_5$ alkoxyl or linear or branched $C_1$-$C_5$ alkyl acyloxy. The substitution of $R^1$ may occur at any position on the benzene ring.

In some embodiments, $R^2$ is hydrogen, methyl, ethyl, linear or branched $C_3$-$C_5$ alkyl, trimethylsilyl, triethylsilyl, tri(linear or branched $C_3$-$C_5$ alkyl)silyl, di-tert-butylphenylsilylortert-butyldimethylsilyl.

The condensation reaction of the invention is asymmetric, and the (1R,2R)-nitroalcohol compound prepared through the method provided herein has a yield of more than 95%, a dr 10:1 and an ee value of more than 97%.

The chiral (1S,2R)-amino alcohol ligand has high diastereoselective and enantioselective catalytic activities, and the method involves mild reaction conditions, simple operation, high yield and desirable optical purity.

The chiral (1S,2R)-amino alcohol ligand used in the invention is presented by structural formula (A):

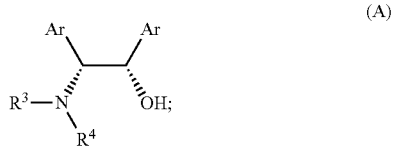

(A)

wherein:
Ar is phenyl, naphthyl or biphenyl;
$R^3$ and $R^4$ are independently hydrogen and linear or branched $C_1$-$C_5$ alkyl, or
$R^3$ and $R^4$ together form 1,3-propylidene, 1,4-butylidene or 1,5-amylidene.

In some embodiments, Ar in the chiral (1S,2R)-amino alcohol ligand of formula (A) is phenyl.

In some embodiments, the chiral (1S,2R)-amino alcohol ligand is (1S,2R)-1,2-diphenyl-2-(pyrrolidin-1-yl)ethan-1-ol, (1S,2R)-2-(dimethylamino)-1,2-diphenylethan-1-ol or (1S,2R)-2-(diisopropylamino)-1,2-diphenylethan-1-ol, which has economical rationality due to the easy preparation and simple recovery. Moreover, these ligands can react with the cupric salt to form corresponding complexes, which can catalyze the condensation reaction with high selectivity to obtain the cis-(1R,2R)-nitroalcohol compound (I).

The cupric salt can combine with the amino alcohol ligand to form a stable complex, and in the invention, the copper complex is formed in situ from the chiral (1S,2R)-amino alcohol ligand and the cupric salt. The cupric salt is an inorganic or organic cupric salt, where the inorganic cupric salt is cupric chloride or cupric bromide, and the organic cupric salt is cupric acetate hydrate, cupric propionate or cupric trifluoromethanesulfonate, preferably cupric acetate hydrate or cupric trifluoromethanesulfonate, and more preferably cupric acetate monohydrate. The monovalent copper salt is also applicable to the reaction system, but it has a poor stability since it is prone to oxidation. Thus, the cupric salt is preferred herein.

In some embodiments, the cupric salt is cupric acetate monohydrate or cupric trifluoromethanesulfonate, which involves a good catalytic effect, high dr and ee values and a wide range of sources.

In some embodiments, the compound of formula (II) is a substituted or unsubstituted benzaldehyde compound, and the compound of formula (III) is nitroethanol or a derivative thereof. In some embodiments, a molar ratio of the compound of formula (II) to the compound of formula (III) to the cupric salt to the chiral (1S,2R)-amino alcohol ligand is 1:1.1-8:0.05-0.15:0.08-0.2, preferably 1: 2-6:0.05-0.15: 0.08-0.2. The amount of nitroethanol or the derivative thereof (III) should be appropriate, since insufficient nitroethanol or the derivative thereof (III) will lead to an incomplete reaction of benzaldehyde (II) and excessive nitroethanol or the derivative thereof (III) may cause a decrease in the dr and ee values of the (1R,2R)-nitroalcohol compound.

The organic solvent used in the asymmetric condensation reaction is generally a polar aprotic solvent, which is preferably selected from the group consisting of toluene, carbon tetrachloride, diethyl ether, tetrahydrofuran, dioxane, dichloromethane, chloroform and ethyl acetate due to extensive sources, low cost, ready availability and simple recovery.

In some embodiments, an asymmetric condensation temperature is −15-15° C. At a temperature far below such range, the yield of the (1R,2R)-nitroalcohol compound may be reduced, while at a temperature much above such range, the enantioselectivity and diastereoselectivity may be lowered. A condensation time is preferably 48-120 h.

After the condensation reaction is completed, the (1R, 2R)-nitroalcohol compound of formula (I) is adjusted to a concentration of 0.5M-0.7M, preferably since the yield will be lowered if the concentration is too low, and an extensively high concentration will lead to poor enantioselectivity and diastereoselectivity.

Compared to the prior art, the invention has the following beneficial effects.

The invention involves readily available raw materials, mild reaction conditions, simple operation, easy recovery of the catalyst and high purity, and thus it is suitable for industrial production.

DETAILED DESCRIPTION OF EMBODIMENTS

As used herein, the term "halogen" refers to fluorine, chlorine, bromine or iodine.

The invention is described in detail below with reference to the embodiments, and these embodiments are not intended to limit the invention.

Example 1

2.0 g of cupric acetate monohydrate (10 mmol), 2.7 g of (1S,2R)-1,2-diphenyl-2-(pyrrolidin-1-yl)ethan-1-ol (10 mmol) and 150 mL of tetrahydrofuran were added in a dry flask. The reaction mixture was stirred at room temperature for 1 h, and then sequentially added with 36.4 g of nitroethanol (400 mmol) and 18.4 g of 4-(methylsulfonyl)benzaldehyde (100 mmol) at −15° C. Then the reaction mixture was reacted at −15° C. under stirring for 48 h. After the reaction was completed, tetrahydrofuran was recovered under vacuum, and the reaction mixture was dropwise added with 100 mL of 5% hydrochloric acid, stirred at room temperature for 20 min and extracted with ethyl acetate three times each for 100 mL. The organic phases were collected, combined, concentrated under vacuum and cooled to room temperature to give 27.0 g of a white crystalline powder (1R,2R)-1-(4-(methylsulfonyl)phenyl)-2-nitropropan-1,3-diol (98% yield, dr=32:1, 98% ee) with a melting point of 136-138° C. and $[\alpha]^{25}_D$ of −32.6 (c=0.29, EtOH).

$^1$H NMR (400 MHz, DMSO): δ 7.93 (d, J=8.0 Hz, 2H), 7.71 (d, J=8.4 Hz, 2H), 6.35 (d, J=4.8 Hz, 1H), 5.28 (dd, $J_1$=6.4 Hz, $J_2$=4.4 Hz, 1H), 5.06 (dd, $J_1$=8.8 Hz, $J_2$=4.8 Hz, 1H), 4.80 (td, $J_1$=9.2 Hz, $J_2$=3.2 Hz, 1H), 3.84-3.77 (m, 1H), 3.25 (dt, $J_1$=12.4 Hz, $J_2$=4.0 Hz, 1H), 3.21 (s, 3H) ppm.

$^{13}$C NMR (100 MHz, DMSO): δ 146.5, 141.1, 128.4, 127.6, 95.4, 71.2, 60.5, 43.9 ppm.

ESI HRMS: $C_{10}H_{13}NO_6S$+Na (calculated: 298.0361; measured: 298.0362).

Example 2

2.0 g of cupric acetate monohydrate (10 mmol), 2.4 g of (1S,2R)-2-(dimethylamino)-1,2-diphenylethan-1-ol (10 mmol) and 200 mL of dioxane were added to a dry flask. The reaction mixture was stirred at room temperature for 1 h, sequentially added with 27.4 g of nitroethanol (300 mmol) and 18.5 g of o-bromobenzaldehyde (100 mmol) at 0° C. and reacted at 0° C. under stirring for 72 h. After the reaction was completed, the dioxane was recovered under vacuum, and the reaction mixture was slowly dropwise added with 100 mL of 5% hydrochloric acid, stirred at room temperature for 20 min and extracted with ethyl acetate three times each for 100 mL. The organic phases were collected, combined, concentrated under vacuum and cooled to room temperature to give 27.1 g of a white crystalline powder (1R,2R)-1-(2-bromophenyl)-2-nitropropan-1,3-diol (98% yield, dr=11:1, 97% ee) with a melting point of 70-73° C. and $[\alpha]_D^{25}$ of −3.3 (c=0.33, EtOH).

$^1$H NMR (400 MHz, CD$_3$OD): 7.61 (dd, $J_1$=8.0 Hz, $J_2$=1.2 Hz, 1H), 7.57 (dd, $J_1$=7.6 Hz, $J_2$=2.0 Hz, 1H), 7.43 (td, $J_1$=7.6 Hz, $J_2$=1.2 Hz, 1H), 7.25 (td, $J_1$=7.6 Hz, $J_2$=2.0 Hz, 1H), 5.49 (d, J=8.4 Hz, 1H), 4.92-4.89 (m, 1H), 4.15-4.09 (m, 1H), 3.43 (dd, $J_1$=12 Hz, $J_2$=3.2 Hz, 1H) ppm.

$^{13}$C NMR (100 MHz, CD$_3$OD): δ 139.0, 132.6, 129.9, 128.5, 127.9, 122.1, 95.3, 70.4, 60.2 ppm.

ESI HRMS: $C_9H_{10}BrNO_4$+Na (calculated: 297.9691; measured: 297.9689).

Example 3

1.6 g of cupric trifluoromethanesulfonate (4.5 mmol), 2.1 g of (1S,2R)-2-(diisopropylamino)-1,2-diphenylethan-1-ol (7.2 mmol) and 130 mL of dichloromethane were added to a dry flask. The reaction mixture was stirred at room temperature for 1 h, sequentially added with 41 g of nitroethanol (450 mmol) and 11.8 g of 4-cyanobenzaldehyde (90 mmol) at −5° C. and reacted under stirring at −5° C. for 96 h. After the reaction was completed, the dichloromethane and nitroethanol were recovered under vacuum, and the reaction mixture was slowly dropwise added 100 mL of 5% hydrochloric acid, stirred at room temperature for 20 min and extracted with ethyl acetate three times each for 80 mL. The organic phases were collected, combined, concentrated under vacuum and cooled to room temperature to give 19.6 g of a white crystalline powder 4-((1R,2R)-1,3-dihydroxy-2-nitropropyl)benzonitrile (98% yield, dr=20:1, 97% ee) with a melting point of 110-111° C. and $[\alpha]_D^{25}$ of −36.4 (c=0.45, EtOH).

$^1$H NMR (400 MHz, CD$_3$OD): δ 7.77-7.74 (m, 2H), 7.63-7.61 (m, 2H), 5.14 (d, J=8.8 Hz, 1H), 4.83-4.78 (m, 1H), 3.86 (dd, $J_1$=12.4 Hz, $J_2$=8.8 Hz, 1H), 3.48 (dd, $J_1$=12.0 Hz, $J_2$=3.2 Hz, 1H) ppm. $^{13}$C NMR (100 MHz, CD$_3$OD): δ 143.8, 130.7, 126.1, 116.5, 110.5, 92.9, 69.8, 58.7 ppm.

ESI HRMS: $C_{28}H_{37}N_5O_9$+Na (calculated: 245.0538; measured: 245.0533).

Example 4

1.0 g of cupric acetate monohydrate (5 mmol), 1.9 g of (1S,2R)-2-(dimethylamino)-1,2-diphenylethan-1-ol (8 mmol) and 200 mL of tetrahydrofuran were added to a dry flask. The reaction mixture was stirred at room temperature for 1 h, sequentially added with 18.3 g of nitroethanol (200 mmol) and 12.4 g of 2-fluorobenzaldehyde (100 mmol) at 10° C. and reacted under stirring at 10° C. for 120 h. After the reaction was completed, the tetrahydrofuran was recovered under vacuum, and the reaction mixture was slowly dropwise added with 100 mL of 5% hydrochloric acid, stirred at room temperature for 20 min and extracted with ethyl acetate three times each for 100 mL. The organic phases were collected, combined, concentrated under vacuum and cooled to room temperature to give 21.1 g of a colorless oil product (1R,2R)-1-(2-fluorophenyl)-2-nitropropan-1,3-diol (98% yield, dr=22.5:1, 99% ee) with $[\alpha]_D^{25}$ of −12.0 (c=0.52, EtOH).

$^1$H NMR (400 MHz, CD$_3$OD): δ 7.55 (td, $J_1$=7.6 Hz, $J_2$=2.0 Hz, 1H), 7.43-7.37 (m, 1H), 7.26 (t, J=7.6 Hz, 1H), 7.17-7.13 (m, 1H), 5.36 (dd, $J_1$=9.2 Hz, $J_2$=3.2 Hz, 1H), 4.96-4.93 (m, 1H), 3.96 (td, $J_1$=12 Hz, $J_2$=2.8 Hz, 1H), 3.96 (dt, $J_1$=12 Hz, $J_2$=3.6 Hz, 1H) ppm.

$^{13}$C NMR (100 MHz, CD$_3$OD): δ 160.9 (d, J=244.0 Hz), 131.3 (d, J=8.5 Hz), 129.3 (d, J=3.9 Hz), 127.6 (d, J=13.2 Hz), 125.6 (d, J=3.4 Hz), 116.1 (d, J=21.4 Hz), 95.6 (d, J=2.5 Hz), 66.9, 61.2 ppm.

ESI HRMS: $C_9H_{10}FNO_4$+Na (calculated: 238.0492; measured: 238.0487).

Example 5

2.0 g of cupric acetate monohydrate (10 mmol), 4.1 g of (1S,2R)-1,2-diphenyl-2-(pyrrolidin-1-yl)ethan-1-ol (15 mmol) and 140 mL of tetrahydrofuran were added to a dry flask. The reaction mixture was stirred at room temperature for 1 h, sequentially added with 36.4 g of nitroethanol (400 mmol) and 13.6 g of 4-methoxybenzaldehyde (100 mmol) at 15° C. and reacted under stirring at 15° C. for 120 h. After the reaction was completed, the tetrahydrofuran was recovered under vacuum, and the reaction mixture was slowly dropwise added with 100 mL of 5% hydrochloric acid, stirred at room temperature for 20 min and extracted with ethyl acetate three times each for 100 mL. The organic phases were collected, combined, concentrated under vacuum and cooled to room temperature to give 21.6 g of a colorless oil product (1R,2R)-1-(4-(methoxy)phenyl)-2-nitropropan-1,3-diol (95% yield, dr=13.7:1, 96% ee) with $[\alpha]_D^{25}$ of −6.9 (c=0.79, EtOH).

$^1$H NMR (400 MHz, CD$_3$OD): δ7.34-7.32 (m, 2H), 6.97-6.95 (m, 2H), 4.94 (d, J=9.6 Hz, 1H), 4.84-4.78 (m, 1H), 3.83-3.79 (m, 4H), 3.36 (dd, $J_1$=12.0 Hz, $J_2$=3.2 Hz, 1H) ppm.

$^{13}$C NMR (100 MHz, CD$_3$OD): δ 161.3, 132.6, 129.0, 115.0, 96.6, 73.1, 61.7, 55.5 ppm.

ESI HRMS: $C_{10}H_{13}NO_5$+Na (calculated: 250.0691; and measured: 250.0683).

Example 6

2.0 g of cupric acetate monohydrate (10 mmol), 4.1 g of (1S,2R)-1,2-diphenyl-2-(pyrrolidin-1-yl)ethan-1-ol (15 mmol) and 180 mL of tetrahydrofuran were added to a dry flask. The reaction mixture was stirred at room temperature for 1 h, sequentially added with 45.5 g of nitroethanol (500 mmol) and 15.2 g of 4-methylthiobenzaldehyde (100 mmol) at 5° C. and reacted under stirring at 5° C. for 120 h. After the reaction was completed, the tetrahydrofuran was recovered under vacuum, and the reaction mixture was slowly dropwise added with 100 mL of 5% hydrochloric acid, stirred at room temperature for 20 min and extracted with ethyl acetate three times each for 100 mL. The organic phases were collected, combined, concentrated under vacuum and cooled to room temperature to give 23.1 g of a colorless oil product (1R,2R)-1-(4-(methylthio)phenyl)-2-nitropropan-1,3-diol (95% yield, dr=10.7:1, 98% ee) with $[\alpha]^{25}_D$ of −22.8 (c=0.64, EtOH).

$^1$H NMR (400 MHz, CD$_3$OD): δ 7.35-7.23 (m, 4H), 4.96 (d, J=9.6 Hz, 1H), 4.84-4.78 (m, 1H), 3.83 (dd, J$_1$=12.0 Hz, J$_2$=9.2 Hz, 1H), 3.39 (dd, J$_1$=12.4 Hz, J$_2$=3.2 Hz, 1H), 2.48 (s, 3H) ppm.

$^{13}$C NMR (100 MHz, CD$_3$OD): δ 139.7, 136.1, 127.1, 126.1, 95.2, 71.9, 60.5, 14.0 ppm.

ESI HRMS: C$_{10}$H$_{13}$NO$_4$S+Na (calculated: 266.0463; measured: 266.0465).

Example 7

1.0 g of cupric acetate monohydrate (5 mmol), 2.7 g of (1S,2R)-1,2-diphenyl-2-(pyrrolidin-1-yl)ethan-1-ol (10 mmol) and 180 mL of tetrahydrofuran were added to a dry flask. The reaction mixture was stirred at room temperature for 1 h, sequentially added with 45.5 g of nitroethanol (500 mmol) and 10.6 g of benzaldehyde (100 mmol) at 0° C. and reacted under stirring at 0° C. for 120 h. After the reaction was completed, the tetrahydrofuran was recovered under vacuum, and the reaction mixture was slowly dropwise added with 100 mL of 5% hydrochloric acid, stirred at room temperature for 20 min and extracted with ethyl acetate three times each for 100 mL. The organic phases were collected, combined, concentrated under vacuum and cooled to room temperature to give 18.7 g of a colorless oil product (1R, 2R)-2-nitro-1-phenylpropan-1,3-diol (95% yield, dr=23:1, 99% ee) with $[\alpha]^{25}_D$ of 2.0 (c=0.79, EtOH).

$^1$H NMR (400 MHz, CDCl$_3$): δ 7.41-7.36 (m, 5H), 5.24 (dd, J$_1$=8.8 Hz, J$_2$=3.2 Hz, 1H), 4.81-4.76 (m, 1H), 3.83-3.72 (m, 2H), 2.85 (d, J=4.0 Hz, 1H), 2.28 (d, J=6.0 Hz, 1H) ppm.

$^{13}$C NMR (100 MHz, CDCl$_3$): δ138.0, 129.4, 129.2, 126.6, 93.8, 72.6, 61.3, ppm.

ESI HRMS: C$_9$H$_{11}$NO$_4$+Na (calculated: 220.0586; measured: 220.0582).

Example 8

2.0 g of cupric acetate monohydrate (10 mmol), 2.4 g of (1S,2R)-2-(dimethylamino)-1,2-diphenylethan-1-ol (10 mmol) and 200 mL of tetrahydrofuran were added to a dry flask. The reaction mixture was stirred at room temperature for 1 h, sequentially added with 27.4 g of nitroethanol (300 mmol) and 12.0 g of 3-methylbenzaldehyde (100 mmol) at 5° C. and reacted under stirring at 5° C. for 72 h. After the reaction was completed, the tetrahydrofuran was recovered under vacuum, and the reaction mixture was slowly dropwise added with 100 mL of 5% hydrochloric acid, stirred at room temperature for 20 min and extracted with ethyl acetate three times each for 100 m. The organic phases were collected, combined, concentrated under vacuum and cooled to room temperature to give 20.7 g of a colorless oil product (1R,2R)-2-nitro-1-(m-methylphenyl)propan-1,3-diol (98% yield, dr=19.7:1, 99% ee) with $[\alpha]_D^{25}$ of −7.4 (c=0.75, EtOH).

$^1$H NMR (400 MHz, CD$_3$OD): δ 7.26 (t, J=7.6 Hz, 1H), 7.22 (t, J=2.0 Hz, 1H), 7.20-7.11 (m, 2H), 4.92 (d, J=9.2 Hz, 1H), 4.82-4.76 (m, 1H), 3.81 (dd, J$_1$=12.4 Hz, J$_2$=9.6 Hz, 1H), 3.33 (dd, J$_1$=12.0 Hz, J$_2$=3.2 Hz, 1H), 2.35 (s, 3H) ppm.

$^{13}$C NMR (100 MHz, CD$_3$OD): δ140.6, 139.5, 130.2, 129.4, 128.2, 124.7, 96.4, 73.5, 61.6, 21.1 ppm.

ESI HRMS: C$_{10}$H$_{13}$NO$_4$+Na (calculated: 234.0742; measured: 234.0733).

Example 9

1.0 g of cupric acetate monohydrate (5 mmol), 2.2 g of (1S,2R)-1,2-diphenyl-2-(pyrrolidin-1-yl)ethan-1-ol (8 mmol) and 180 mL of tetrahydrofuran were added to a dry flask. The reaction mixture was stirred at room temperature for 1 h, sequentially added with 36.4 g of nitroethanol (400 mmol) and 17.4 g of 4-(trifluoromethyl)benzaldehyde (100 mmol) at 0° C. and reacted under stirring at 0° C. for 48 h. After the reaction was completed, the tetrahydrofuran was recovered under vacuum, and the reaction mixture was slowly dropwise added with 100 mL of 5% hydrochloric acid, stirred at room temperature for 20 min and extracted with ethyl acetate three times each for 100 mL. The organic phases were collected, combined, concentrated under vacuum and cooled to room temperature to give 25.5 g of a colorless oil product (1R,2R)-2-nitro-1-(4-(trifluoromethyl)phenyl)propan-1,3-diol (96% yield, dr=10:1, 97% ee) with $[\alpha]^{25}_D$ of −14.7 (c=1.0, EtOH).

$^1$H NMR (400 MHz, CD$_3$OD): δ 7.70 (d, J=8.0 Hz, 2H, syn), 7.62 (d, J=8.0 Hz, 2H, syn), 5.13 (d, J=9.2 Hz, 1H), 4.82 (td, J$_1$=9.2 Hz, J$_2$=3.2 Hz, 1H), 3.86 (dd, J$_1$=12.0 Hz, J$_2$=8.8 Hz, 1H, syn), 3.45 (dd, J$_1$=12.4 Hz, J$_2$=3.2 Hz, 1H, syn) ppm.

$^{13}$C NMR (100 MHz, CD$_3$OD): δ142.6, 128.8 (q, J=32 Hz), 125.8, 123.7 (q, J=4 Hz), 122.6 (q, J=269 Hz), 93.2, 69.9, 58.7 ppm.

ESI HRMS: C$_{10}$H$_{10}$F$_3$NO$_4$+Na (calculated: 288.0460; measured: 288.0465).

Example 10

2.0 g of cupric acetate monohydrate (10 mmol), 3.3 g of (1S,2R)-1,2-diphenyl-2-(pyrrolidin-1-yl)ethan-1-ol (12 mmol) and 200 mL of tetrahydrofuran were added to a dry flask. The reaction mixture was stirred at room temperature for 1 h, sequentially added with 36.4 g of nitroethanol (400 mmol) and 18.2 g of 4-phenylbenzaldehyde (100 mmol) at 5° C. and reacted under stirring at 5° C. for 72 h. After the reaction was completed, the tetrahydrofuran was recovered under vacuum, and the reaction mixture was slowly dropwise added with 100 mL of 5% hydrochloric acid, stirred at room temperature for 20 min and extracted with ethyl acetate three times each for 100 mL. The organic phases were collected, combined, concentrated under vacuum and cooled to room temperature to give 26.5 g of a white crystalline powder (1R,2R)-1-([1,1'-biphenyl]-4-yl)-2-nitropropan-1,3-diol (97% yield, dr=12.8:1, 99% ee) with a melting point of 122-126° C. and $[\alpha]^{25}_D$ of −24.3 (c=1.0, EtOH).

$^1$H NMR (400 MHz, CD$_3$OD): δ 7.58-7.49 (m, 4H), 7.38 (d, J=8.0 Hz, 2H), 7.32 (t, J=8.0 Hz, 2H), 7.26-7.21 (m, 1H), 4.95 (d, J=9.2 Hz, 1H), 4.80-4.75 (m, 1H), 3.78 (dd, J$_1$=12.0 Hz, J$_2$=9.2 Hz, 1H), 3.34 (dd, J$_1$=12.0 Hz, J$_2$=3.2 Hz, 1H) ppm.

$^{13}$C NMR (100 MHz, CD$_3$OD): δ 141.5, 140.3, 138.6, 128.5, 127.2, 127.1, 127.0, 126.6, 95.2, 72.1, 60.5 ppm.

ESI HRMS: C$_{15}$H$_{15}$NO$_4$+Na (calculated: 296.0899; measured: 296.0894).

Example 11

2.0 g of cupric acetate monohydrate (10 mmol), 2.7 g of (1S,2R)-1,2-diphenyl-2-(pyrrolidin-1-yl)ethan-1-ol (10 mmol) and 180 mL of tetrahydrofuran were added to a dry flask. The reaction mixture was stirred at room temperature for 1 h, sequentially added with 36.4 g of nitroethanol (400 mmol) and 16.4 g of 4-acetoxybenzaldehyde (100 mmol) at 0° C. and reacted under stirring at 0° C. for 60 h. After the reaction was completed, the tetrahydrofuran was recovered under vacuum, slowly dropwise added with 100 mL of 5% hydrochloric acid, stirred at room temperature for 20 min and extracted with ethyl acetate three times each for 100 mL. The organic phases were collected, combined, concentrated under vacuum and cooled to room temperature to give 24.5 g of a colorless oil product 4-((1R,2R)-1,3-dihydroxy-2-nitropropyl)phenyl acetate (96% yield, dr=16:1, 99% ee) with $[\alpha]^{25}_D$ of −17.6 (c=1.0, EtOH).

$^1$H NMR (400 MHz, CD$_3$OD): δ 7.46-7.44 (m, 2H), 7.15-7.13 (m, 2H), 5.04 (d, J=9.2 Hz, 1H), 4.84 (td, J$_1$=9.2 Hz, J$_2$=3.2 Hz, 1H), 3.85 (dd, J$_1$=12.4 Hz, J$_2$=9.6 Hz, 1H), 3.42 (dd, J$_1$=12.4 Hz, J$_2$=3.2 Hz, 1H), 2.27 (s, 3H) ppm.

$^{13}$C NMR (100 MHz, CD$_3$OD): δ 171.0, 152.1, 138.2, 128.8, 122.9, 96.2, 72.7, 61.5, 20.7 ppm.

ESI HRMS: C$_{11}$H$_{13}$NO$_6$+Na (calculated: 278.0641; measured: 278.0640).

Example 12

2.0 g of cupric acetate monohydrate (10 mmol), 2.7 g of (1S,2R)-1,2-diphenyl-2-(pyrrolidin-1-yl)ethan-1-ol (10 mmol) and 180 mL of tetrahydrofuran were added to a dry flask. The reaction mixture was stirred at room temperature for 1 h, sequentially added with 36.4 g of nitroethanol (400 mmol) and 14.1 g of 2-chlorobenzaldehyde (100 mmol) at 0° C. and reacted under stirring at 0° C. for 84 h. After the reaction was completed, the tetrahydrofuran was recovered under vacuum, slowly dropwise added with 100 mL of 5% hydrochloric acid, stirred at room temperature for 20 min and extracted with ethyl acetate three times each for 100 mL. The organic phases were collected, combined, concentrated under vacuum and cooled to room temperature to give 22.7 g of a colorless oil product (1R,2R)-1-(2-chlorophenyl)-2-nitropropan-1,3-diol (98% yield, dr=11.1:1, 97% ee) with $[\alpha]^{25}_D$ of −11.4 (c=1.0, EtOH).

$^1$H NMR (400 MHz, CD$_3$OD): δ 7.63 (dd, J$_1$=7.6 Hz, J$_2$=2.0 Hz, 1H), 7.47-7.34 (m, 3H), 5.57 (d, J=8.4 Hz, 1H), 4.99-4.94 (m, 1H), 4.14 (dd, J$_1$=12.0 Hz, J$_2$=9.6 Hz, 1H), 3.51 (dd, J$_1$=12.0 Hz, J$_2$=3.2 Hz, 1H) ppm.

$^{13}$C NMR (100 MHz, CD$_3$OD): δ 138.2, 133.1, 130.6, 130.2, 129.2, 128.4, 96.0, 69.0, 61.1 ppm.

ESI HRMS: C$_9$H$_{10}$ClNO$_4$+Na (calculated: 254.0196; measured: 254.0193).

Example 13

2.0 g of cupric acetate monohydrate (10 mmol), 2.7 g of (1S,2R)-1,2-diphenyl-2-(pyrrolidin-1-yl)ethan-1-ol (10 mmol) and 200 mL of tetrahydrofuran were added to a dry flask, The reaction mixture was stirred at room temperature for 1 h, sequentially added with 61.6 g of tert-butyldimethyl (2-nitroethoxy)silane (300 mmol) and 18.4 g of 4-methylsulfonylbenzaldehyde (100 mmol) at 0° C. and reacted under stirring at 0° C. for 84 h. After the reaction was completed, the tetrahydrofuran was recovered under vacuum, and the reaction mixture was slowly dropwise added with 100 mL of 5% hydrochloric acid, stirred at room temperature for 20 min and extracted with ethyl acetate three times each for 100 mL. The organic phases were collected, combined, concentrated under vacuum and cooled to room temperature to give 38.2 g of a white crystalline powder (1R,2R)-3-((tert-butyldimethylsilyl)oxy)-1-(4-(methanesulfonyl)phenyl)-2-nitropropan-1-ol (98% yield, dr=20:1, 97% ee) with a melting point of 98-100° C. and $[\alpha]^{25}_D$ of −2.4 (c=1.0, EtOH).

$^1$H NMR (400 MHz, CD$_3$OD): δ 7.98 (d, J=8.4 Hz, 2H), 7.71 (d, J=8.0 Hz, 2H), 5.22 (d, J=8.8 Hz, 1H), 4.86-4.81 (m, 1H), 3.95 (dd, J$_1$=11.6 Hz, J$_2$=8.4 Hz, 1H), 3.61 (dd, J$_1$=11.6 Hz, J$_2$=2.8 Hz, 1H), 3.13 (s, 3H), 0.83 (s, 9H), 0.02 (s, 6H) ppm.

$^{13}$C NMR (100 MHz, CD$_3$OD): δ 146.0, 140.8, 127.7, 127.4, 94.2, 71.0, 61.7, 42.9, 24.7, 17.5, −6.9, −7.0 ppm.

ESI HRMS: C$_{16}$H$_{27}$NO$_6$SSi+Na (calculated: 412.1226; measured: 412.1223).

Described above are merely some preferred embodiments of the invention, and it should be understood that the invention is not limited thereto. Any combinations, modifications and changes made without departing from the spirit of the invention, shall fall within the scope of the invention defined by the appended claims.

What is claimed is:

1. A method of synthesizing a (1R,2R)-nitroalcohol compound of formula (I), comprising:
subjecting a compound of formula (II) and a compound of formula (III) to a condensation reaction in an organic solvent in the presence of a copper complex generated in situ from a chiral (1S,2R)-amino alcohol ligand and a cupric salt to produce the (1R,2R)-nitroalcohol compound of formula (I), as shown in the following reaction scheme:

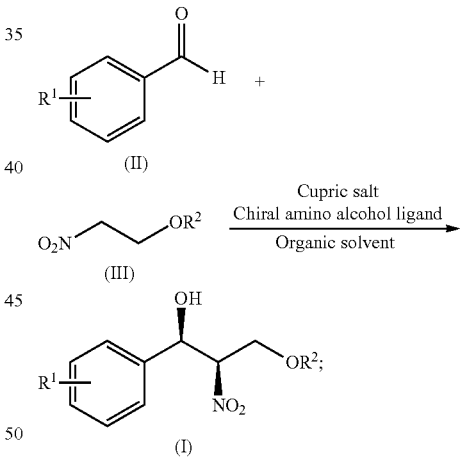

wherein:
R$^1$ is hydrogen, methylsulfonyl, bromo, cyano, fluoro, methoxy, methylthio, methyl, trifluoromethyl, phenyl, acetoxy, or chloro; and
R$^2$ is hydrogen or tert-butyl dim ethyl silyl;
the chiral (1S,2R)-amino alcohol ligand is (1S,2R)-2-(diisopropylamino)-1,2-diphenyl ethan-1-ol;
the cupric salt is cupric acetate monohydrate or cupric trifluoromethanesulfonate; and
the condensation reaction is performed at −15-15° C. for 48-120 h.

2. The method of claim 1, wherein a molar ratio of the compound of formula (II) to the compound of formula (III) to the cupric salt to the chiral (1S,2R)-amino alcohol ligand is 1:1.1-8:0.05-0.15:0.08-0.2.

3. The method of claim 2, wherein a molar ratio of the compound of formula (II) to the compound of formula (III) to the cupric salt to the chiral (1S,2R)-amino alcohol ligand is 1: 2-6:0.05-0.15:0.08-0.2.

4. The method of claim 1, wherein the organic solvent is a polar aprotic solvent.

5. The method of claim 2, wherein the organic solvent is a polar aprotic solvent.

6. The method of claim 3, wherein the organic solvent is a polar aprotic solvent.

7. The method of claim 4, wherein the polar aprotic solvent is selected from the group consisting of toluene, carbon tetrachloride, diethyl ether, tetrahydrofuran, dioxane, dichloromethane, chloroform and ethyl acetate.

8. The method of claim 5, wherein the polar aprotic solvent is selected from the group consisting of toluene, carbon tetrachloride, diethyl ether, tetrahydrofuran, dioxane, dichloromethane, chloroform and ethyl acetate.

9. The method of claim 6, wherein the polar aprotic solvent is selected from the group consisting of toluene, carbon tetrachloride, diethyl ether, tetrahydrofuran, dioxane, dichloromethane, chloroform and ethyl acetate.

\* \* \* \* \*